United States Patent [19]

Emmers et al.

[11] Patent Number: 6,159,667

[45] Date of Patent: *Dec. 12, 2000

[54] THERMOGRAPHIC RECORDING MATERIAL WITH IMPROVED IMAGE TONE AND/OR STABILITY UPON THERMAL DEVELOPMENT

[75] Inventors: Sabine Emmers, Lommel; Bartholomeus Horsten, Rumst; Ingrid Geuens, Ranst; Yvan Gilliams, Hever; André Bellens, Pulle; Dirk Bollen, Sint-Truiden; Ivan Hoogmartens, Wilrijk, all of Belgium

[73] Assignee: Agfa-Gevaert, Mortsel, Belgium

[*] Notice: This patent is subject to a terminal disclaimer.

[21] Appl. No.: 09/271,652

[22] Filed: Mar. 17, 1999

Related U.S. Application Data

[62] Division of application No. 08/982,318, Dec. 10, 1997, Pat. No. 6,096,486.
[60] Provisional application No. 60/038,769, Feb. 20, 1997.

[30] Foreign Application Priority Data

Dec. 10, 1996 [EP] European Pat. Off. ............... 96203498

[51] Int. Cl.$^7$ ..................................................... G03C 1/498
[52] U.S. Cl. .............................................................. 430/350
[58] Field of Search ..................................... 430/618, 620, 430/617, 350, 564

[56] References Cited

U.S. PATENT DOCUMENTS 3,856,527  12/1974  Hamb et al. .
3,897,935   8/1975  Forster et al. .
4,152,162   5/1979  Masuda et al. .
4,273,723   6/1981  Hayashi et al. .

*Primary Examiner*—Thorl Chea
*Attorney, Agent, or Firm*—Baker Botts L.L.P.

[57] ABSTRACT

A recording material comprising a support and a thermosensitive element containing silver behenate, an organic reducing agent therefor in thermal working relationship therewith and a binder, wherein the silver behenate is not associated with mercury and/or lead ions and when the recording material is irradiated with a copper K$\alpha_1$ X-ray source the ratio, normalized to a quantity of silver in the recording material of 1 g per m$^2$ thereof, of the sum of the peak heights of the X-ray diffraction lines attributable to silver behenate at Bragg angles, 2$\Theta$, of 6.01°, 7.56°, 9.12°, 10.66°, 12.12° and 13.62° to the sum of the peak heights of the X-ray diffraction lines at Bragg angles, 2$\Theta$, of 25.60°, 35.16° and 43.40° of NIST standard 1976, rhombohedral Al$_2$O$_3$, determined with the same X-ray diffractometer in the same state of adjustment, is greater than 0.85; production processes for particles of substantially light-insensitive organic silver salt comprising silver behenate with these X-ray characteristics in the presence and substantial absence of organic solvent.

13 Claims, No Drawings

THERMOGRAPHIC RECORDING MATERIAL WITH IMPROVED IMAGE TONE AND/OR STABILITY UPON THERMAL DEVELOPMENT

This is a divisional of application Ser. No. 08/982,318 filed Dec. 10, 1997, U.S. Pat. No. 6,096,486.

This application claims the benefit of U.S. Provisional Application No. 60/038,769 filed Feb. 20, 1997.

DESCRIPTION

1. Field of the Invention

The present invention relates to a thermographic recording material suitable for thermal development. In particular, it concerns improvements in the image tone upon imagewise thermal development thereof and archivability and light stability of the thermographic prints thereof.

2. Background of the Invention

Thermal imaging or thermography is a recording process wherein images are generated by the use of thermal energy.

In direct thermal thermography a visible image pattern is formed by image-wise heating of a recording material containing matter that by chemical or physical process changes colour or optical density. Such recording materials become photothermographic upon incorporating a photosensitive agent which after exposure to UV, visible or IR light is capable of catalyzing or participating in a thermographic process bringing about changes in colour or optical density.

Most of the "direct" thermographic recording materials are of the chemical type. On heating to a certain conversion temperature, an irreversible chemical reaction takes place and a coloured image is produced.

According to U.S. Pat. No. 3,080,254 a typical heat-sensitive (thermographic) copy paper includes in the heat-sensitive layer a thermoplastic binder, a water-insoluble silver salt and an appropriate organic reducing agent. Thermo-sensitive copying paper is used in "front-printing" or "back-printing" using infra-red radiation absorbed and transformed into heat in contacting infra-red light absorbing image areas of an original as illustrated in FIGS. 1 and 2 of U.S. Pat. No. 3,074,809.

GB-A 1,378,734 discloses a process of producing a silver salt of an organic carboxylic acid, which comprises mixing (a) an aqueous solution of silver nitrate or a silver complex with (b) a solution of an organic carboxylic acid in a solvent in which the organic carboxylic acid is soluble, both the silver salt of an organic carboxylic acid and silver nitrate being almost insoluble and with which water is sparingly miscible, so as to react the organic carboxylic acid with silver ions, the reaction being conducted in the presence of a soluble mercury compound and/or a soluble lead compound.

EP-A 754 969, published after the priority date of the present application, discloses a process for producing a suspension of particles containing a substantially light-insensitive silver salt of an organic carboxylic acid, comprising simultaneous metered addition of an aqueous solution or suspension of an organic carboxylic acid or its salt; and an aqueous solution of a silver salt to an aqueous liquid, wherein the metered addition of the aqueous solution or suspension of the organic carboxylic acid or its salt; and/or the aqueous solution of the silver salt is regulated by the concentration of silver ions or the concentration of anions of the silver salt in the aqueous liquid.

Research Disclosure number 17029, published in June 1978, in section II gives a survey of different methods of preparing organic heavy metal salts. Method 5, for example, describes the preparation of silver behenate by (a) heating behenic acid in water to a temperature above the melting point of the acid, but below the boiling point of the dispersion, (b) adding an aqueous solution of alkali metal or ammonium hydroxide, and (c) adding an aqueous solution of silver nitrate. However, in order to obtain a fine emulsion of an organic heavy metal salt, either the synthesis has to be carried out in an organic solvent medium as disclosed, for example, in U.S. Pat. No. 3,700,458 or in a mixture of water and a substantially water insoluble organic solvent as disclosed, for example, in U.S. Pat. No. 3,960,908 for silver carboxylates.

The association of silver behenate with mercury or lead ions, particularly mercury ions, as disclosed in GB 1,378,734 is environmentally undesirable and infringes governmental regulations. Direct thermal recording materials with silver behenates produced using the processes described in RD 17029 upon image-wise heating exhibit a brown image colour which is undesirable for medical images viewed in transmission with a viewing box. This lack of image colour neutrality can be quantified by spectrophotometric measurements according to ASTM Norm E179-90 in a R(45/0) geometry with evaluation according to ASTM Norm E308-90 to produce the CIELAB $a^*$ and $b^*$ coordinates. Colour neutrality on the basis of CIELAB-values corresponds to $a^*$ and $b^*$ values of zero, with a negative $a^*$-value indicating a greenish image-tone becoming greener as $a^*$ becomes more negative, a positive $a^*$-value indicating a reddish image-tone becoming redder as $a^*$ becomes more positive, a negative $b^*$-value indicating a bluish image-tone becoming bluer as $b^*$ becomes more negative and a positive $b^*$-value indicating a yellowish image-tone becoming yellower as $b^*$ becomes more positive.

OBJECTS OF THE INVENTION

It is therefore an object of the invention to provide a thermographic recording material, which on imagewise thermal development produces an image with a perceptibly bluer image tone.

It is a further object of the present invention to provide a thermographic and photothermographic recording materials whose prints exhibit improved archivability and light stability.

It is a still further object of the present invention to provide production processes for substantially light-insensitive organic silver salt comprising silver behenate.

Further objects and advantages of the invention will become apparent from the description hereinafter.

SUMMARY OF THE INVENTION

Surprisingly it has been found that thermographic recording materials comprising a support and a thermosensitive element comprising silver behenate with a higher crystallinity, an organic reducing agent therefor in thermal working relationship therewith and a binder exhibit a perceptibly bluer image tone upon imagewise thermal development and/or produces thermographic prints with improved archivability and/or improved light stability, when silver behenate is present therein with a substantially increased crystallinity over prior art materials.

The above mentioned object is realised with a recording material comprising a support and a thermosensitive element containing silver behenate, an organic reducing agent therefor in thermal working relationship therewith and a binder, wherein the silver behenate is not associated with mercury and/or lead ions and when the recording material is irradiated with a copper $K\alpha_1$ X-ray source the ratio, normalized to a quantity of silver in the recording material of 1 g per $m^2$ thereof, of the sum of the peak heights of the X-ray diffraction lines attributable to silver behenate at Bragg angles, 2Θ, of 6.01°, 7.56°, 9.12°, 10.66°, 12.12° and 13.62° to the sum of the peak heights of the X-ray diffraction lines at Bragg angles, 2Θ, of 25.60°, 35.16° and 43.40° of NIST standard 1976, rhombohedral $Al_2O_3$. determined with the same X-ray diffractometer in the same state of adjustment, is greater than 0.85.

A recording process is also provided according to the present invention comprising the steps of: (i) bringing an outermost layer of the above described recording material in proximity with a heat source; and (ii) applying heat from the heat source imagewise heating to the recording material while maintaining proximity to the heat source to produce an image; and (iii) removing the recording material from the heat source.

A production process for particles of substantially light-insensitive organic silver salt comprising silver behenate is also provided according to the present invention comprising the steps of: i) producing a solution or dispersion, A, comprising an alkali metal or ammonium salt of an organic compound with at least one acidic hydrogen atom comprising behenic acid in a mixture of water and an organic solvent at a temperature at which the particles of substantially light-insensitive organic silver salt comprising silver behenate do not undergo reduction; and ii) adding a quantity of an aqueous solution, B, of a silver salt containing an equal number of silver ions to the alkali or ammonium ions in the solution or dispersion A; characterized in that the initial mixing number during the addition of the aqueous solution B to the solution or dispersion A is greater than or equal to $2\times10^{-4}$ during the production of the particles of substantially light-insensitive organic silver salt comprising silver behenate, the mixing number being the ratio of the molar rate at which the silver salt is supplied to the solution A in a reactor to the molar rate at which the alkali or ammonium salt is circulated in the reactor.

A production process for a dispersion of particles of substantially light-insensitive organic silver salt including silver behenate in an aqueous medium is further provided according to the present invention comprising the steps of: i) producing an aqueous dispersion of one or more organic acids including behenic acid and an anionic surfactant; ii) substantially neutralizing the organic acids with aqueous alkali thereby forming organic acid salts including a behenic acid salt; (iii) adding an aqueous solution of a silver salt to completely convert the organic acid salt(s) into their silver salts including silver behenate, characterized in that the anionic surfactant is present in a molar ratio with respect to organic acid greater than 0.15 and the silver salt is added at a rate between 0.025 mol/mol organic silver salt.min and 2.25 mol/mol organic silver salt.min.

Preferred embodiments of the invention are disclosed in the dependent claims.

DETAILED DESCRIPTION OF THE INVENTION

In a preferred embodiment of the recording process, according to the present invention, the heat source is a thermal head with a thin film thermal head being particularly preferred.

Thermosensitive Element

The thermosensitive element, according to the present invention, comprises silver behenate, an organic reducing agent therefor in thermal working relationship therewith and a binder. The element may contain a layer system in which the ingredients may be dispersed in different layers, with the proviso that the two ingredients are in reactive association with one another i.e. during the thermal development process the reducing agent must be present in such a way that it is able to diffuse to the silver behenate so that reduction of silver behenate to silver can occur giving the desired image-tone.

In a preferred embodiment of the present invention the thermosensitive element further comprises a photosensitive species capable upon exposure of forming a species capable of catalyzing reduction of the silver behenate.

Silver Behenate Characterization

The silver behenate in the recording material, of the present invention, wherein when irradiated with a copper $K\alpha_1$ X-ray source the ratio, normalized to a quantity of silver in the recording material of 1 g per $m^2$ thereof, of the sum of the peak heights of the X-ray diffraction lines attributable to silver behenate at Bragg angles, 2Θ, of 6.01°, 7.56°, 9.12°, 10.66°, 12.12° and 13.62° to the sum of the peak heights of the X-ray diffraction lines at Bragg angles, 2Θ, of 25.60°, 35.16° and 43.40° of NIST (National Institute of Standards, Gaithersburg, Md. 20899-0001, USA) standard 1976, rhombohedral $Al_2O_3$, determined with the same X-ray diffractometer in the same state of adjustment, is greater than 0.85. In a preferred embodiment of the present invention, the normalized ratio, as defined above, is greater than 1.0 and in a particularly preferred embodiment is greater than 1.2.

The normalized ratio is obtained by determining X-ray diffraction spectra on sheets of a particular recording material and of the NIST standard 1976 cut to fit the sample holder of the X-ray diffractometer used, subtracting the background using standard techniques, determining the peak heights of the diffraction peaks, determining for the sample of recording material the sum of the peak heights, $K_{material}$, of the XRD lines attributable to silver behenate at Bragg angles, 2Θ, of 6.01°, 7.56°, 9.12°, 10.66°, 12.12° and 13.62°, determining for the sample of NIST standard 1976 the sum of the peak heights, $K_{1976}$, of the X-ray diffraction lines at Bragg angles, 2Θ, of 25.60°, 35.16° and 43.40°, calculating the ratio of $K_{material}/K_{1976}$ for the recording material, determining the concentration of silver $C_{Ag}$ present in the recording material in grams per square meter of material and finally normalizing the ratio $K_{material}/K_{1976}$ with $C_{Ag}$ to give the normalized ratio $K_{material}/(K_{1976}\times C_{Ag})$, which is referred to in the detailed description of the present invention as the crystallinity of silver behenate.

The concentration of silver present in the recording material can be determined by any known technique e.g. non-destructive methods such as X-ray fluorescence and destructive methods such as dissolution of the silver salt followed by standard volumetric techniques for the determination of silver, such as described in R. Belcher and A. J. Nutten, Quantitative Inorganic Analysis, 2nd Edition, Butterworths, London (1960), pages 201–219.

A standard test was used to assess the image tone of thermographic recording materials comprising silver behenate of the present invention. This consisted of first coating a subbed 175 μm thick polyethylene terephthalate support with a solvent dispersion comprising: silver behenate (AgB), 400% by weight of relative to AgB of polyvinylbutyral, 50 mol % relative to AgB of ethyl 3,4-dihydroxybenzoate, 15 mol % relative to AgB of benzo[e][1,3]oxazine-2,4-dione, 5 mol % relative to AgB of 7-(ethylcarbonato)benzo[e][1,3] oxazine-2,4-dione, 0.9 wt % of silicone oil relative to AgB, 5 mol % relative to AgB of tetrachlorophthalic anhydride, 21.98 mol % relative to AgB of adipic acid and 10 mol % relative to AgB of benzotriazole to a coating weight of AgB of about 5 g/m$^2$. After drying for 1 hour at 50° C., the thermographic recording material was tempered for 7 days at 45° C. Thermal printing was carried out with the print head separated from the thermosensitive layer by a separable 5 μm thick polyethylene terephthalate ribbon coated successively with a subbing layer, heat-resistant layer and a slipping layer (anti-friction layer) and a printer equipped with a thin film thermal head with a resolution of 300 dpi and operated with a line time of 19 ms (the line time being the time needed for printing one line). During the line time the print head received constant power. The average printing power, being the total amount of electrical input energy during one line time divided by the line time and by the surface area of the heat-generating resistors was 1.5 mJ/dot. The image tone was assessed both by visual inspection and on the basis of the L*, a* and b* CIELAB-values of the image as a function of the optical density of the image determined with a MACBETH™ TR924 densitometer. The L*, a* and b* CIELAB-values were determined by spectrophotometric measurements according to ASTM Norm E179-90 in a R(45/0) geometry with evaluation according to ASTM Norm E308-90. The value of b* at the minimum in the dependence of b* upon image density of less than −2.0 was found to correspond with an image with a blue tone compared with images with a brown tone for minima with higher b* values.

Compounds for Promoting Silver Behenate Crystallinity

Non-halide ion containing phosphonium compounds have been found to promote the crystallinity of silver behenate. Preferred non-halide ion containing phosphonium compounds for promoting silver behenate crystallinity according to the present invention are:

PC01=(2-methoxyethyl)triphenylphosphonium toluenesulphonate

PC02=ethyltriphenylphosphonium toluenesulphonate

PC03=(2-triphenylphosphonium) ethyltriphenylphosphonium benzenesulphonate

Silver Behenate

The silver behenate of the present invention is not associated with mercury and/or lead ions. This means that mercury/and or silver ions are not intentionally added at any point during the preparation process and therefore are not intentionally associated with the silver behenate in the recording material of the present invention.

Silver Behenate Preparation in Solvent/Water Media

Any known synthesis technique and any known dispersion technique can be used to produce the silver behenate of the present invention with the provision that the silver behenate in the thermographic recording material of the present invention fulfils the above criteria.

In a preferred embodiment of the recording material of the present invention, the silver behenate is present in the thermosensitive element as particles of substantially light-insensitive organic silver salt comprising the silver behenate.

The above described production process for particles of substantially light-insensitive organic silver salt comprising silver behenate is characterized in that the mixing number during the addition of the aqueous solution B to the solution or dispersion A is greater than or equal to $2 \times 10^{-4}$ during the production of the particles of substantially light-insensitive organic silver salt comprising silver behenate, the mixing number being the ratio of the molar rate at which the silver salt is supplied to the solution A in a reactor to the molar rate at which the alkali or ammonium salt is circulated in the reactor. The mixing number can be expressed as follows:

$$\text{mixing number,} \quad MN = MN_0 \times \frac{1 + \frac{dV_B}{dt} \times \frac{t}{V_0}}{1 - \frac{C_B}{M_0} \times \frac{dV_B}{dt} \times t}$$

$$\text{where:} \quad MN_0 = \frac{\frac{dV_B}{dt} \times C_B}{\frac{M_0}{V_0} \times G_F \times D^3 \times n}$$

$$\frac{dV_B}{dt} = \text{rate of addition of solution } B \text{ in dm}^3 / \text{minute}$$

$C_B$ = concentration of solution B in moles/dm$^3$ $M_0$ = initial quantity of alkali metal or ammonium salt of an organic compound with at least one acidic hydrogen atom comprising behenic acid present in solution A in moles $V_0$ = volume of solution A in the reactor in dm$^3$ $G_F$ = pumping number of the stirrer in the reactor n = stirring rate in rotations/minute D = stirrer diameter in dm t = time in minutes The pumping number of the stirrer in a reactor is the ratio of stirrer pumping rate to the product of the stirrer diameter cubed and the stirring rate (n×D$^3$) and is dependent on a variety of factors, such as the ratio of stirrer to reactor diameter, the off-bottom clearance ratio of the stirrer and the Reynolds number of the stirrer, see for example A. Bakker and L. E. Gates, Chemical Engineering Progress pages 25 to 34 (December 1995) and Nagata, "Mixing Principles and Applications", J. Wiley & Sons, New York (1975), pages 136–139.

The mathematical nature of the above function for the mixing number is such that the mixing number will always increase as the preparation of the particles of organic silver salt comprising silver behenate proceeds.

In a preferred production process, according to the present invention, the solution or dispersion A has a molar concentration of alkali metal or ammonium salt of organic compound with at least one acidic hydrogen atom comprising behenic acid in the mixture of water and an organic solvent greater than 0.022.

In another preferred production process, according to the present invention, the organic solvent is present at between 20 and 80% by weight of the mixture and preferably between 35 and 65% by weight of the mixture. In further preferred production process the organic solvent is 2-butanone.

Surprisingly it has been found from scanning electron micrographs of dispersions of particles of organic silver salt comprising silver behenate and from transition electron micrographs of thin slices of thermosensitive layers coated from dispersions of particles of organic silver salt comprising silver behenate that the shape of these particles in general changes from rods to a more globular shape as the mixing number is increased and that this change in particle morphology is accompanied by an increase in the crystallinity, as defined above, provided that the dispersion of these particles of organic silver salt comprising silver behenate is carried out under similar conditions. In a preferred embodiment of the recording material of the present invention at least 20% by weight of the particles of organic silver salt comprising silver behenate is present as globular particles and in a particularly preferred embodiment of the recording material of the present invention at least 40% by weight of the particles of organic silver salt comprising silver behenate is present as globular particles.

Preparation of Aqueous Dispersions of Silver Behenate-Containing Particles in the Substantial Absence of Solvent A production process for a dispersion of particles of substantially light-insensitive organic silver salt including silver behenate in an aqueous medium is provided according to the present invention comprising the steps of: i) producing an aqueous dispersion of one or more organic acids including behenic acid and a salt of an alkylarylsulfonate; ii) substantially neutralizing the organic acids with aqueous alkali thereby forming organic acid salts including a behenic acid salt; (iii) adding an aqueous solution of a silver salt to completely convert the organic acid salts into their silver salts including silver behenate, characterized in that the anionic surfactant is present in a molar ratio with respect to organic acid greater than 0.15 and the silver salt is added at a rate between 0.025 mol/mol organic silver salt.min and 2.25 mol/mol organic silver salt.min. In preferred embodiments of the production process for a dispersion of particles of substantially light-insensitive organic silver salt including silver behenate in an aqueous medium the anionic surfactant is present in a molar ratio with respect to organic carboxylic acid greater than 0.25 and the silver salt is added at a rate between 0.03 mol/mol organic silver salt.min and 0.7 mol/mol organic silver salt.min, with a molar ratio of anionic surfactant with respect to organic acid greater than 0.3 and a rate of silver salt addition of between 0.04 mol/mol organic silver salt.min and 0.3 mol/mol organic silver salt.min being particularly preferred.

In a preferred embodiment step (iii) of the production process of the present invention is carried out such that part the solution of acid salts produced in step (ii) of the process is present in the reaction vessel prior to silver salt solution addition and part thereof is added simultaneously with the addition of the silver salt solution, with about 25 to 50% of the solution of acid salts produced in step (ii) being in the reaction vessel prior to silver salt addition being particularly preferred.

In another preferred embodiment of the production process for a dispersion of particles of substantially light-insensitive organic silver salt including silver behenate in an aqueous medium the anionic surfactant is selected from the group consisting of: alkylsulfonate salts, alkarylsulfonate salts, aralkylsulfonate salts, arylsulfonate salts, alkylsulfate salts, aralkylsulfate salts, arylsulfate salts, alkarylsulfate salts and organic carboxylate salts. In a particularly preferred embodiment of the present invention the anionic surfactant is an alkarylsulfonate salt and in an especially preferred embodiment the anionic surfactant is an alkylbenzene sulfonate salt. Suitable anionic surfactants for use in the production process for a dispersion of particles of substantially light-insensitive organic silver salt including silver behenate in an aqueous medium according to the present invention are:

Surfactant Nr. 1=MARLON™ A-396, a sodium alkylphenylsulfonate from Hüls;
Surfactant Nr. 2=Marlon™ A-53, an alkylphenylsulfonic acid from Hüls neutralized with an alkali hydroxide;
Surfactant Nr. 3=ammonium 4-dodecylbenzene sulfonate;
Surfactant Nr. 4=ULTRAVON™ W, a sodium arylsulfonate from Ciba-Geigy;
Surfactant Nr. 5=ERKANTOL™ BX, a sodium diisopropylnaphthalenesulfonate from BAYER;
Surfactant Nr. 6=ALKANOL™ XC, a sodium nonylnaphthalenesulfonate from DU PONT;
Surfactant Nr. 7=HOSTAPUR™, a secondary alkanesulfonate from HOECHST;
Surfactant Nr. 8=MERSOLAT™ H80, a sodium hexadecylsulfonate from Bayer;
Surfactant Nr. 9=HOSTAPAL™ B, a sodium trisalkylphenylpolyethyleneglycol (EO 7-8) sulphate from Hoechst;
Surfactant Nr. 10=TERGITOL™ 4, a sodium 1-(2'-ethylbutyl)-4-ethylhexylsulphate from GOLDSCHMIDT;

The above-described production process for a dispersion of particles of substantially light-insensitive organic silver salt including silver behenate in an aqueous medium the pH used must be sufficiently low to avoid the oxidation of silver ions to silver oxide or silver hydroxide for which a pH below 10 is usually required, the process temperature is chosen such that it is above the melting point of the organic acid(s) used which in the case of behenic acid means a temperature of about 80 to 85° C., must be carried out with stirring, the stirring rate being dependent upon the size of the stirrer relative to the reaction vessel, the type of stirrer used, avoidance of silver oxide or silver hydroxide formation due to insufficient mixing and avoidance of foaming, and being usually between 200 and 1000 rpm and a slight excess of an organic acid, for example behenic acid with e.g. 2 mol % excess being preferred.

The size of the silver acid salts particles containing silver behenate can be varied by varying the rate of silver salt addition, the concentration of anionic surfactant and the temperature, the equivalent diameter of the particles increasing with decreasing addition rate, decreasing anionic surfactant concentration and increasing temperature.

In a further preferred embodiment production of the process for a dispersion of particles of substantially light-insensitive organic silver salt including silver behenate in an aqueous medium according to the present invention the production process also includes a step in which the silver organic salt including silver behenate is subject to ultrafiltration. The ultrafiltration process removes ionic species and concentrates the silver behenate dispersion by filtration through a cartridge-filter with a pore size sufficiently small to remove the salt produced upon the formation of the organic silver salt without removing the silver behenate. Cartridge-filters with 10,000 to 500,000 MW have been found to be suitable for this purpose. In order to maintain the stability of the silver behenate dispersion during ultrafiltration it is necessary to maintain a minimum anionic surfactant concentration, but the counterion of the anionic surfactant can be changed, should the presence of the original counterion be undesirable in the thermographic recording material. For example the sodium ions in Surfactant nr 1 can be replaced by ammonium ions by washing with an ammonium nitrate solution during the ultrafiltration process and the sodium ion concentration reduced to below 100 ppm.

Substantially Light-Insensitive Organic Silver Salt Dispersions

Should it be necessary to produce dispersions with particles of organic silver salt comprising silver behenate with higher crystallinity, as defined above, it has been found that thermographic recording materials, according to the present invention, can be produced, if dispersions thereof are produced using dispersion techniques in which the particles themselves are subjected to as little damage as possible commensurate with achieving a satisfactory dispersion quality. The use of microfluidizers, ultrasonic apparatuses, rotor stator mixers etc. have been found to be useful in this regard.

Surfactants and Dispersion Agents

Surfactants and dispersants aid the dispersion of ingredient or reactants which are insoluble in the particular dispersion medium. The thermographic recording materials of the present invention may contain one or more surfactants, which may be anionic, non-ionic or cationic surfactants and/or one or more dispersants.

Suitable dispersants are natural polymeric substances, synthetic polymeric substances and finely divided powders, for example finely divided non-metallic inorganic powders such as silica. Suitable hydrophilic natural or synthetic polymeric substances contain one or more hydroxyl, carboxyl or phosphate groups, e.g. protein-type binders such as gelatin, casein, collagen, albumin and modified gelatin; modified cellulose; starch; modified starch; modified sugars; modified dextrans etc. Examples of suitable hydrophilic synthetic polymeric substances are polyvinylalcohol; polyvinylpyrrolidone; polyacrylic acid; and polymethacrylic acid and their copolymers.

Reducing Agents

Suitable organic reducing agents for the reduction of the substantially light-insensitive organic heavy metal salts are organic compounds containing at least one active hydrogen atom linked to O, N or C, such as is the case with, aromatic di- and trihydroxy compounds; aminophenols; METOL (tradename); p-phenylenediamines; alkoxynaphthols, e.g. 4-methoxy-1-naphthol described in U.S. Pat. No. 3,094,41; pyrazolidin-3-one type reducing agents, e.g. PHENIDONE (tradename); pyrazolin-5-ones; indan-1,3-dione derivatives; hydroxytetrone acids; hydroxytetronimides; hydroxylamine derivatives such as for example described in U.S. Pat. No. 4,082,901; hydrazine derivatives; and reductones e.g. ascorbic acid; see also U.S. Pat. Nos. 3,074,809, 3,080,254, 3,094,417 and 3,887,378.

Among useful aromatic di- and tri-hydroxy compounds having at least two hydroxy groups in ortho- or para-position on the same aromatic nucleus, e.g. benzene nucleus, hydroquinone and substituted hydroquinones, catechol, pyrogallol, gallic acid and gallic acid esters are preferred. Particularly useful are polyhydroxy spirobis-indane compounds.

Among the catechol-type reducing agents, i.e. reducing agents containing at least one benzene nucleus with two hydroxy groups (—OH) in ortho-position, the following are preferred: catechol, 3-(3,4-dihydroxyphenyl) propionic acid, 1,2-dihydroxybenzoic acid, gallic acid and esters e.g. methyl gallate, ethyl gallate, propyl gallate, tannic acid, and 3,4-dihydroxy-benzoic acid esters. Particularly preferred catechol-type reducing agents, are described in EP-B 692 733 and unpublished European Patent Application EP 97202872.4.

Other suitable reducing agents, particularly for photothermographic recording materials, are sterically hindered phenols, bisphenols and sulfonamidophenols.

Combinations of reducing agents may also be used that on heating become reactive partners in the reduction of the substantially light-insensitive organic silver salt comprising silver behenate. For example, combinations of reducing agents with sulfonamidophenols are described in the periodical Research Disclosure, February 1979, item 17842, in U.S. Pat. Nos. 4,360,581 and 4,782,004, and in EP-A 423 891 and combinations of sterically hindered phenols with sulfonyl hydrazide reducing agents such as disclosed in U.S. Pat. No. 5,464,738; trityl hydrazides and formyl-phenyl-hydrazides such as disclosed in U.S. Pat. No. 5,496,695; trityl hydrazides and formyl-phenyl-hydrazides with diverse auxiliary reducing agents such as disclosed in U.S. Pat. No. 5,545,505, U.S. Pat. No. 5,545,507 and U.S. Pat. No. 5,558,983; acrylonitrile compounds as disclosed in U.S. Pat. No. 5,545,515 and U.S. Pat. No. 5,635,339; and 2-substituted malondialdehyde compounds as disclosed in U.S. Pat. No. 5,654,130.

Organic reducing metal salts, e.g. stannous stearate, have also been used in such reducing agent combinations, as disclosed in U.S. Pat. Nos. 3,460,946 and 3,547,648. Sterically hindered phenols and bisphenols have themselves been used in such reducing agent combinations, such as described in U.S. Pat. No. 4,001,026 and U.S. Pat. No. 3,547,648 respectively.

The silver image density depends on the coverage of the above defined reducing agent(s) and organic silver salt(s) and has to be preferably such that, on heating above 100° C., an optical density of at least 2.5 can be obtained. Preferably at least 0.10 moles of reducing agent per mole of organic silver salt is used.

Polycarboxylic Acids and Anhydrides Thereof

According to the recording material of the present invention the thermosensitive element may comprise in addition at least one polycarboxylic acid and/or anhydride thereof in a molar percentage of at least 20 with respect to all the organic silver salt(s) present and in thermal working relationship therewith. The polycarboxylic acid may be aliphatic (saturated as well as unsaturated aliphatic and also cycloaliphatic) or an aromatic polycarboxylic acid. These acids may be substituted e.g. with alkyl, hydroxyl, nitro or halogen. They may be used in anhydride form or partially esterified on the condition that at least two free carboxylic acids remain or are available in the heat recording step.

Particularly suitable are saturated aliphatic dicarboxylic acids containing at least 4 carbon atoms, e.g.: succinic acid, glutaric acid, adipic acid, pimelic acid, suberic acid, azelaic acid, sebacic acid, nonane-dicarboxylic acid, decane-dicarboxylic acid, undecanedicarboxylic acid.

Suitable unsaturated dicarboxylic acids are: maleic acid, citraconic acid, itaconic acid and aconitic acid. Suitable polycarboxylic acids are citric acid and derivatives thereof, acetonedicarboxylic acid, iso-citric acid and α-ketoglutaric acid.

Preferred aromatic polycarboxylic acids are ortho-phthalic acid and 3-nitro-phthalic acid, tetrachlorophthalic acid, mellitic acid, pyromellitic acid and trimellitic acid and the anhydrides thereof.

Film-Forming Binders of the Thermosensitive Element

The film-forming binder of the thermosensitive element containing the substantially light-insensitive organic heavy metal salt may be all kinds of natural, modified natural or synthetic resins or mixtures of such resins, wherein the organic heavy metal salt can be dispersed homogeneously: e.g. cellulose derivatives such as ethylcellulose, cellulose esters, e.g. cellulose nitrate, carboxymethylcellulose, starch ethers, galactomannan, polymers derived from α,β-ethylenically unsaturated compounds such as polyvinyl chloride, after chlorinated polyvinyl chloride, copolymers of vinyl chloride and vinylidene chloride, copolymers of vinyl chloride and vinyl acetate, polyvinyl acetate and partially hydrolyzed polyvinyl acetate, polyvinyl alcohol, polyvinyl acetals that are made from polyvinyl alcohol as starting material in which only a part of the repeating vinyl alcohol units may have reacted with an aldehyde, preferably polyvinyl butyral, copolymers of acrylonitrile and acrylamide, polyacrylic acid esters, polymethacrylic acid esters, polystyrene and polyethylene or mixtures thereof.

A particularly suitable polyvinyl butyral containing a minor amount of vinyl alcohol units is marketed under the trade name BUTVAR™ B79 of Monsanto USA and provides a good adhesion to paper and properly subbed polyester supports.

The layer containing the organic silver salt is commonly coated onto a support in sheet- or web-form from an organic solvent containing the binder dissolved therein, but may also be applied from an aqueous medium containing a water-dispersible binder and/or a water dispersible binder.

Suitable water-soluble film-forming binders for use in thermographic and photothermographic recording materials according to the present invention are: polyvinyl alcohol, polyacrylamide, polymethacrylamide, polyacrylic acid, polymethacrylic acid, polyvinylpyrrolidone, polyethyleneglycol, proteinaceous binders such as gelatin, modified gelatins such as phthaloyl gelatin, polysaccharides, such as starch, gum arabic and dextran and water-soluble cellulose derivatives. A preferred water-soluble binder for use in the thermographic and photothermographic recording materials of the present invention is gelatin.

Suitable water-dispersible binders for use in the thermographic and photothermographic recording materials of the present invention may be any water-insoluble polymer e.g. water-insoluble cellulose derivatives, polyurethanes, polyesters polycarbonates and polymers derived from $\alpha,\beta$-ethylenically unsaturated compounds such as afterchlorinated polyvinyl chloride, partially hydrolyzed polyvinyl acetate, polyvinyl alcohol, polyvinyl acetals preferably polyvinyl butyral, and homopolymers and copolymers produced using monomers selected from the group consisting of: vinyl chloride, vinylidene chloride, acrylonitrile, acrylamides, methacrylamides. methacrylates, acrylates, methacrylic acid, acrylic acid, vinyl esters, styrenes, dienes and alkenes; or mixtures thereof. It should be noted that there is no clear cut transition between a polymer dispersion and a polymer solution in the case of very small polymer particles resulting in the smallest particles of the polymer being dissolved and those slightly larger being in dispersion.

Preferred water-dispersible binders for use according to the present invention are water-dispersible film-forming polymers with covalently bonded ionic groups selected from the group consisting of sulfonate, sulfinate, carboxylate, phosphate, quaternary ammonium, tertiary sulfonium and quaternary phosphonium groups. Further preferred water-dispersible binders for use according the the present invention are water-dispersible film-forming polymers with covalently bonded moieties with one or more acid groups.

Water-dispersible binders with crosslinkable groups, e.g. epoxy groups, aceto-acetoxy groups and crosslinkable double bonds are also preferred.

Preferred water-dispersible binders for use in the thermographic and photothermographic recording materials of the present invention are polymer latexes. For use as a latex the dispersible polymer has preferably some hydrophilic functionality. Polymers with hydrophilic functionality for forming an aqueous polymer dispersion (latex) are described e.g. in U.S. Pat. No. 5,006,451, but serve therein for forming a barrier layer preventing unwanted diffusion of vanadium pentoxide present as an antistatic agent.

Binder to Organic Silver Salt Ratio

The binder to organic silver salt weight ratio is preferably in the range of 0.2 to 6, and the thickness of the recording layer is preferably in the range of 5 to 50 $\mu$m.

Thermal Solvent

The above mentioned binders or mixtures thereof may be used in conjunction with waxes or "heat solvents" also called "thermal solvents" or "thermosolvents" improving the reaction speed of the redox-reaction at elevated temperature. By the term "heat solvent" in this invention is meant a non-hydrolyzable organic material which is in solid state in the recording layer at temperatures below 50° C. but becomes a plasticizer for the recording layer in the heated region and/or liquid solvent for at least one of the redox-reactants, e.g. the reducing agent for the organic heavy metal salt, at a temperature above 60° C.

Toning Agent

In order to obtain a neutral black image tone in the higher densities and neutral grey in the lower densities the recording layer contains preferably in admixture with the organic heavy metal salts and reducing agents a so-called toning agent known from thermography or photothermography.

Suitable toning agents are the phthalimides and phthalazinones within the scope of the general formulae described in U.S. Pat. No. 4,082,901. Further reference is made to the toning agents described in U.S. Pat. Nos. 3,074,809, 3,446, 648 and 3,844,797. Other particularly useful toning agents are the heterocyclic toner compounds of the benzoxazine dione or naphthoxazine dione type as disclosed in GB-P 1,439,478, U.S. Pat. No. 3,951,660 and U.S. Pat. No. 5,599,647. A toner compound particularly suited for use in combination with polyhydroxy benzene reducing agents is 3,4-dihydro-2,4-dioxo-1,3,2H-benzoxazine described in U.S. Pat. No. 3,951,660.

Other Additives

The recording layer may contain in addition to the ingredients mentioned above other additives such as free fatty acids, surface-active agents, antistatic agents, e.g. non-ionic antistatic agents including a fluorocarbon group as e.g. in $F_3C(CF_2)_6CONH(CH_2CH_2O)$—H, silicone oil, e.g. BAYSILONE™ Ol A (from BAYER AG, GERMANY), ultraviolet light absorbing compounds, white light reflecting and/or ultraviolet radiation reflecting pigments and/or optical brightening agents.

Support

The support for the thermal imaging material according to the present invention may be transparent, translucent or opaque, e.g. having a white light reflecting aspect and is preferably a thin flexible carrier made e.g. from paper, polyethylene coated paper or transparent resin film, e.g. made of a cellulose ester, e.g. cellulose triacetate, polypropylene, polycarbonate or polyester, e.g. polyethylene terephthalate. For example, a paper base substrate is present which may contain white reflecting pigments, optionally also applied in an interlayer between the recording material and the paper base substrate.

The support may be in sheet, ribbon or web form and subbed if need be to improve the adherence to the thereon coated thermosensitive recording layer. The support may be made of an opacified resin composition, e.g. polyethylene terephthalate opacified by means of pigments and/or microvoids and/or coated with an opaque pigment-binder layer, and may be called synthetic paper, or paperlike film; information about such supports can be found in EP's 194 106 and 234 563 and U.S. Pat. Nos. 3,944,699, 4,187,113, 4,780,402 and 5,059,579. Should a transparent base be used, the base may be colourless or coloured, e.g. having a blue colour.

One or more backing layers may be provided to control physical properties such as curl and static.

Outermost Layer

The outermost layer of the recording material may in different embodiments of the present invention be the outermost layer of the thermosensitive element, a protective layer applied to the thermosensitive element or a layer on the opposite side of the support to the thermosensitive element.

Protective Layer

According to a preferred embodiment of the recording material, according to the present invention, the thermosensitive element is coated with a protective layer to avoid local deformation of the thermosensitive element and to improve resistance against abrasion.

The protective layer preferably comprises a binder, which may be solvent-soluble, solvent-dispersible, water-soluble or water-dispersible. Among the solvent-soluble binders polycarbonates as described in EP-A 614 769 are particularly preferred. However, water-soluble or water-dispersible binders are preferred for the protective layer, as coating can be performed from an aqueous composition and mixing of the protective layer with the immediate underlayer can be avoided by using a solvent-soluble or solvent-dispersible binder in the immediate underlayer.

A protective layer according to the present invention may comprise in addition a thermomeltable particle optionally with a lubricant present on top of the protective layer as described in WO 94/11199. In a preferred embodiment at least one solid lubricant having a melting point below 150° C. and at least one liquid lubricant in a binder is present, wherein at least one of the lubricants is a phosphoric acid derivative.

Water-Soluble or Water-Dispersible Binder for Outermost Layer

According to an embodiment of the present invention the outermost layer of the recording material may comprise a water-soluble binder, a water-dispersible binder or a mixture of a water-soluble and a water-soluble binder. Suitable water-soluble binders for the outermost layer are, for example, gelatin, polyvinylalcohol, cellulose derivatives or other polysaccharides, hydroxyethylcellulose, hydroxypropylcellulose etc., with hardenable binders being preferred and polyvinylalcohol being particularly preferred. Suitable water-dispersible binders are polymeric latexes.

Crosslinking Agents for Outermost Layer

The outermost layer according to the present invention may be crosslinked. Crosslinking can be achieved by using crosslinking agents such as described in WO 95/12495 for protective layers, e.g. tetra-alkoxysilanes, polyisocyanates, zirconates, titanates, melamine resins etc., with tetraalkoxysilanes such as tetramethylorthosilicate and tetraethylorthosilicate being preferred.

Matting Agents for Outermost Layer

The outermost layer of the recording material according to the present invention may comprise a matting agent. Suitable matting agents are described in WO 94/11198 and include e.g. talc particles and optionally protrude from the outermost layer.

Lubricants for Outermost Layer

Solid or liquid lubricants or combinations thereof are suitable for improving the slip characteristics of the recording materials according to the present invention.

Solid lubricants which can be used according to the present invention are polyolefin waxes, ester waxes, polyolefin-polyether block copolymers, amide waxes, polyglycols, fatty acids, fatty alcohols, natural waxes and solid phosphoric acid derivatives. Preferred solid lubricants are thermomeltable particles such as those described in WO 94/11199.

Liquid lubricants which can be used according to the present invention according to the present invention are fatty acid esters such as glycerine trioleate, sorbitan monooleate and sorbitan trioleate, silicone oil derivatives and phosphoric acid derivatives.

Photosensitive Species

A preferred photosensitive species capable upon exposure of forming species capable of catalyzing reduction of the silver behenate of the present invention is silver halide.

The photosensitive silver halide used in the present invention may be employed in a range of 0.1 to 100 mol percent; preferably, from 0.2 to 80 mol percent; particularly preferably from 0.3 to 50 mol percent; especially preferably from 0.5 to 35 mol %; and especially from 1 to 12 mol % of substantially light-insensitive organic silver salt.

The silver halide may be any photosensitive silver halide such as silver bromide, silver iodide, silver chloride, silver bromoiodide, silver chlorobromoiodide, silver chlorobromide etc.

The silver halide may be in any form which is photosensitive including, but not limited to, cubic, orthorhombic, tabular, tetrahedral, octagonal etc. and may have epitaxial growth of crystals thereon.

The silver halide used in the present invention may be employed without modification. However, it may be chemically sensitized with a chemical sensitizing agent such as a compound containing sulphur, selenium, tellurium etc., or a compound containing gold, platinum, palladium, iron, ruthenium, rhodium or iridium etc., a reducing agent such as a tin halide etc., or a combination thereof. The details of these procedures are described in T. H. James, "The Theory of the Photographic Process", Fourth Edition, Macmillan Publishing Co. Inc., New York (1977), Chapter 5, pages 149 to 169.

Spectral Sensitizers

The recording material, according to the present invention, may contain an infra-red sensitizer, an ultra-violet light sensitizer or a visible light sensitizer. Suitable sensitizers include cyanine, merocyanine, styryl, hemicyanine, oxonol, hemioxonol and xanthene dyes. Useful cyanine dyes include those having a basic nucleus, for example a thiazoline nucleus, an oxazoline nucleus, a pyrroline nucleus, a pyridine nucleus, an oxazole nucleus, a thiazole nucleus, a selenazole nucleus and an imidazole nucleus. Preferred merocyanine dyes include those having not only the above described basic nuclei but also acid nuclei, for example a thiohydantoin nucleus, a rhodanine nucleus, an oxazolidinedione nucleus, a thiazolidinedione nucleus, a barbituric acid nucleus, a thiazolinone nucleus, a malononitrile nucleus and a pyrazolone nucleus. Of the above described cyanine and merocyanine dyes, those having imino groups or carboxyl groups are particularly preferred.

Suitable infra-red sensitizers include those disclosed in EP-A's 465 078, 559 101, 616 014 and 635 756, JN's 03-080251, 03-163440, 05-019432, 05-072662 and 06-003763 and U.S. Pat. Nos. 4,515,888, 4,639,414, 4,713, 316, 5,258,282 and 5,441,866.

Supersensitizers

According to the present invention the recording material further includes a supersensitizer. Preferred supersensitzers are selected from the group of compounds consisting of: mercapto-compounds, disulfide-compounds, stilbene compounds, organoborate compounds and styryl compounds. Suitable supersensitizers for use with infra-red spectral sensitizers are disclosed in EP-A 559 228, EP-A 587 338, U.S. Pat. No. 3,877,943, U.S. Pat. No. 4,873,184 and unpublished European Patent Application EP 96202107.7.

Antihalation Dyes

In addition to the ingredients, the recording materials used in the present invention may also contain antihalation or acutance dyes which absorb light which has passed through the photosensitive thermally developable photographic material, thereby preventing its reflection. Such dyes may be incorporated into the photosensitive thermally developable photographic material or in any other layer of the photographic material of the present invention.

Antistatic Layer

In a preferred embodiment the recording material of the present invention an antistatic layer is applied to the outermost layer not comprising at least one solid lubricant having a melting point below 150° C. and at least one liquid lubricant in a binder, wherein at least one of the lubricants is a phosphoric acid derivative.

Coating

The coating of any layer of the recording material of the present invention may proceed by any coating technique e.g. such as described in Modern Coating and Drying Technology, edited by Edward D. Cohen and Edgar B. Gutoff, (1992) VCH Publishers Inc. 220 East 23rd Street, Suite 909 New York, N.Y. 10010, U.S.A.

Thermographic Processing

Thermographic imaging is carried out by the image-wise application of heat either in analogue fashion by direct exposure through an image of by reflection from an image, or in digital fashion pixel by pixel either by using an infra-red heat source, for example with a Nd-YAG laser or other infra-red laser, with a thermographic material preferably containing an infra-red absorbing compound, or by direct thermal imaging with a thermal head.

In thermal printing image signals are converted into electric pulses and then through a driver circuit selectively transferred to a thermal printhead. The thermal printhead consists of microscopic heat resistor elements, which convert the electrical energy into heat via Joule effect. The electric pulses thus converted into thermal signals manifest themselves as heat transferred to the surface of the thermal paper wherein the chemical reaction resulting in colour development takes place. Such thermal printing heads may be used in contact or close proximity with the recording layer. The operating temperature of common thermal printheads is in the range of 300 to 400° C. and the heating time per picture element (pixel) may be less than 1.0 ms, the pressure contact of the thermal printhead with the recording material being e.g. 200–500 g/cm² to ensure a good transfer of heat.

In order to avoid direct contact of the thermal printing heads with a recording layer not provided with an outermost protective layer, the image-wise heating of the recording layer with the thermal printing heads may proceed through a contacting but removable resin sheet or web wherefrom during the heating no transfer of recording material can take place.

The image signals for modulating the laser beam or current in the micro-resistors of a thermal printhead are obtained directly e.g. from opto-electronic scanning devices or from an intermediary storage means, e.g. magnetic disc or tape or optical disc storage medium, optionally linked to a digital image work station wherein the image information can be processed to satisfy particular needs.

Activation of the heating elements can be power-modulated or pulse-length modulated at constant power. The image-wise heating can be carried out such that heating elements not required to produce an image pixel generate an amount of heat ($H_e$) in accordance with the following formula:

$$0.5\ H_D < H_e < H_D$$

wherein $H_D$ represents the minimum amount of heat required to cause visible image formation in the thermographic recording material.

EP-A 654 355 describes a method for making an image by image-wise heating by means of a thermal head having energizable heating elements, wherein the activation of the heating elements is executed duty cycled pulsewise. When used in thermographic recording operating with thermal printheads the thermographic recording materials are not suitable for reproducing images with fairly large number of grey levels as is required for continuous tone reproduction. EP-A 622 217 discloses a method for making an image using a direct thermal imaging element producing improvements in continuous tone reproduction.

Image-wise heating of the thermographic recording material can also be carried out using an electrically resistive ribbon incorporated into the material. Image- or pattern-wise heating of the thermographic recording material may also proceed by means of pixel-wise modulated ultra-sound, using e.g. an ultrasonic pixel printer as described e.g. in U.S. Pat. No. 4,908,631.

Photothermographic Processing

Photothermographic recording materials, according to the present invention, may be exposed with radiation of wavelength between an X-ray wavelength and a 5 microns wavelength with the image either being obtained by pixel-wise exposure with a finely focused light source, such as a CRT light source; a UV, visible or IR wavelength laser, such as a He/Ne-laser or an IR-laser diode, e.g. emitting at 780 nm, 830 nm or 850 nm; or a light emitting diode, for example one emitting at 659 nm; or by direct exposure to the object itself or an image therefrom with appropriate illumination e.g. with UV, visible or IR light.

For the thermal development of image-wise exposed photothermographic recording materials, according to the present invention, any sort of heat source can be used that enables the recording materials to be uniformly heated to the development temperature in a time acceptable for the application concerned e.g. contact heating, radiative heating, microwave heating etc.

Industrial Application

Direct thermal imaging can be used for both the production of transparencies and reflection type prints. Application of the present invention is envisaged in the fields of both graphics images requiring high contrast images with a very steep print density applied dot energy dependence and continuous tone images requiring a weaker print density applied dot energy dependence, such as required in the medical diagnostic field. In the hard copy field recording materials on a white opaque base are used, whereas in the medical diagnostic field black-imaged transparencies are widely used in inspection techniques operating with a light box.

While the present invention will hereinafter be described in connection with a preferred embodiment thereof, it will be understood that it is not intended to limit the invention to that embodiment. On the contrary, it is intended to cover all alternatives, modifications, and equivalents as may be included within the spirit and scope of the invention as defined by the appending claims.

The invention is illustrated hereinafter by way of invention examples and comparative examples. The percentages and ratios given in these examples are by weight unless otherwise indicated. The ingredients used in the invention and comparative examples, other than those mentioned above, are:

as organic silver salt:
  AgB=silver behenate;
as binders:
  PVB=BUTVAR™ B79, a polyvinyl butyral from Monsanto;
  K7598=type K7598, a calcium-free gelatin from Koepff;
  LATEX 01=a latex of a copolymer of 50% by weight of butadiene and 50% by weight of methyl methacrylate;
  LATEX 02=a latex of a terpolymer of 47.5% by weight of butadiene, 47.5% by: weight of methyl methacrylate and 5% by weight of itaconic acid;
as reducing agents:
  R01=ethyl 3,4-dihydroxybenzoate;
  R02=3(3',4'-dihydroxyphenyl)propionic acid
as toning agents:
  TA01=benzo[e][1,3]oxazine-2,4-dione;
  TA02=7-(ethylcarbonato)-benzo[e][1,3]oxazine-2,4-dione (see formula II below)

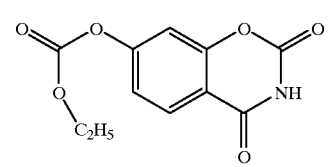

(II)

TA03=succinimide;
TA04=phthalazinone;
TA05=phthalazine;
as levelling agent:
  oil=Baysilone™, a silicone oil from Bayer AG;
as stabilizers:
  S01=tetrachlorophthalic anhydride;
  S02=adipic acid;
  S03=benzotriazole.

INVENTION EXAMPLES 1 to 7 and
COMPARATIVE EXAMPLES 1 to 3

Preparation of Silver Behenate

The silver behenate types A to C of COMPARATIVE EXAMPLES 1 to 3 and silver behenate types I to VII of INVENTION EXAMPLES 1 to 7 were prepared by dissolving the required quantity of behenic acid in 2-butanone at 60° C. with vigorous stirring followed by adding demineralized water while maintaining the reactor at a temperature of between 56 and 60° C., converting the behenic acid into sodium behenate, in the quantity and at the concentration specified in tables 1 and 2 for the COMPARATIVE and INVENTION EXAMPLES respectively, by adding an aqueous solution of sodium hydroxide with vigorous stirring while maintaining the temperature of the reactor at a temperature between 56 and 60° C. and finally converting the sodium behenate into silver behenate by adding the quantity of silver nitrate specified for the specific EXAMPLE and silver behenate type in tables 1 and 2 for the COMPARATIVE and INVENTION EXAMPLES respectively as an aqueous solution, with the concentration specified for the specific EXAMPLE and silver behenate type in tables 1 and 2 for the COMPARATIVE and INVENTION EXAMPLES respectively, at the rate specified for the specific EXAMPLE and silver behenate type in tables 1 and 2 for the COMPARATIVE and INVENTION EXAMPLES respectively with vigorous stirring while maintaining the reactor temperature at the temperature given for the specific EXAMPLE and silver behenate type in tables 1 and 2 for the COMPARATIVE and INVENTION EXAMPLES respectively. The final percentage by weight of 2-butanone in the suspending mixture of 2-butanone and water and the initial mixing number for the specific EXAMPLE and silver behenate type are also given in tables 1 and 2 for the COMPARATIVE and INVENTION EXAMPLES respectively.

TABLE 1

| Comparative example number | AgB type | sodium behenate quantity [moles] | sodium behenate concentration* [M] | silver nitrate quantity [moles] | silver nitrate concentration [M] | final % by weight 2-butanone | temperature [° C.] | AgNO$_3$ addition time [min] | initial mixing number MN$_o$ |
|---|---|---|---|---|---|---|---|---|---|
| 1 | A | 180 | 0.248 | 180 | 0.4 | 23 | 65 | 240 | $9.5 \times 10^{-5}$ |
| 2 | B | 180 | 0.248 | 180 | 0.4 | 23 | 65 | 240 | $9.5 \times 10^{-5}$ |
| 3 | C | 180 | 0.248 | 180 | 0.4 | 23 | 65 | 240 | $9.5 \times 10^{-5}$ |

*initial concentration

TABLE 2

| Invention example number | AgB type | sodium behenate quantity [moles] | sodium behenate concentration* [M] | silver nitrate quantity [moles] | silver nitrate concentration [M] | final % by weight 2-butanone | temperature [° C.] | AgNO$_3$ addition time [min] | initial mixing number MN$_o$ |
|---|---|---|---|---|---|---|---|---|---|
| 1 | I | 0.245 | 0.097 | 0.245 | 1.75 | 45 | 55 | $3^+ + 55^x$ | $1.09 \times 10^{-3}$ |
| 2 | II | 110.9 | 0.100 | 110.9 | 1.67 | 45 | 55 | $3^+ + 15^x$ | $5.29 \times 10^{-3}$ |
| 3 | III | 0.25 | 0.183 | 0.25 | 1.88 | 45 | 60 | 0.75 | $4.73 \times 10^{-3}$ |
| 4 | IV | 151.4 | 0.194 | 151.4 | 5.91 | 45 | 55 | 1.5 | $1.60 \times 10^{-2}$ |
| 5 | V | 0.5 | 0.158 | 0.5 | 3.76 | 45 | 55 | $1.5^+ + 11^x$ | $2.74 \times 10^{-3}$ |

TABLE 2-continued

| | | sodium behenate | | silver nitrate | | final | | AgNO₃ | initial |
|---|---|---|---|---|---|---|---|---|---|
| Invention example number | AgB type | quantity [moles] | concentration* [M] | quantity [moles] | concentration [M] | % by weight 2-butanone | temperature [° C.] | addition time [min] | mixing number MN₀ |
| 6 | VI | 98 | 0.087 | 98 | 5.91 | 45 | 55 | 1.08 | $2.92 \times 10^{-2}$ |
| 7 | VII | 3.066 | 0.085 | 3.066 | 1.67 | 40 | 55 | 119 | $2.20 \times 10^{-4}$ |

*initial concentration
⁺first half of AgNO₃
ˣsecond half of AgNO₃

INVENTION EXAMPLES 8 to 15 and COMPARATIVE EXAMPLES 4 to 6

Dispersions of Silver Behenate in 2-butanone

The dispersions of COMPARATIVE EXAMPLE 4, COMPARATIVE EXAMPLE 5 and INVENTION EXAMPLE 9 were obtained by ball milling for 120 hours 56.5 g of the dried silver behenate powders of COMPARATIVE EXAMPLE 1, COMPARATIVE EXAMPLE 2 and INVENTION EXAMPLE 1 respectively in a solution of 56.5 g of PVB in 387.5 g of 2-butanone.

The dispersions of COMPARATIVE EXAMPLE 6 and INVENTION EXAMPLES 8 and 10 to 15 were obtained by first preparing a predispersion of 56.5 g of the dried silver behenate powders of COMPARATIVE EXAMPLE 3 and INVENTION EXAMPLES 1 to 7, as given below in tables 3 and 4, in a solution of 56.5 g of PVB in 387.5 g of 2-butanone by stirring for 10 minutes with an Ultra-Turrax™ stirrer. These predispersions were then microfluidized by passing them once through a MICROFLUIDICS™ M-110Y high pressure microfluidizer at a jet pressure of 400 bar to produce the dispersions of COMPARATIVE EXAMPLE 6 and INVENTION EXAMPLES 8 and 10 to 15.

Coating of Recording Materials

A subbed polyethylene terephthalate support having a thickness of 175 μm was doctor blade-coated from a coating composition containing 2-butanone as a solvent using the above-described silver behenate dispersions and the additional ingredients given below so as to obtain thereon, after drying for 1 hour at 50° C., layers with the compositions given in table 3 for COMPARATIVE EXAMPLES 4 to 6 with silver behenate types A to C respectively, prepared according to COMPARATIVE EXAMPLES 1 to 3 respectively, and table 4 for INVENTION EXAMPLES 8 to 15 with silver behenate types I to VII as indicated therein, prepared according to INVENTION EXAMPLES 1 to 7.

Determination of the Crystallinity of Silver Behenate in the Recording Materials The crystallinity of the silver behenate in the recording materials of the recording materials of COMPARATIVE EXAMPLES 4 to 6 and INVENTION EXAMPLES 8 to 15 were determined as follows:

i) 30 mm diameter samples of the recording materials of COMPARATIVE EXAMPLES 4 to 6 and INVENTION EXAMPLES 8 to 15 and of NIST standard 1976 were cut from larger sheets using a punch;

ii) X-ray diffraction scans were then carried out using a SIEMENS D5000 X-ray diffractometer equipped with a copper $K\alpha_1$ X-ray source operating at 40 keV and a current of 30 mA with the samples in the sample holder thereof to scan the samples of COMPARATIVE EXAMPLES 4 to 6, INVENTION EXAMPLES 8 to 15 and NIST standard 1976, with the same X-ray diffractometer in exactly the same state of adjustment, in steps of 0.05 degrees at a rate of 1 step/s between Bragg angles, 2Θ, of 5° and 50° and the data processed using SIEMENS DIFFRAC™ AT software to produce X-ray diffraction spectra corrected for background and exact peak heights of each X-ray diffraction peak. Five X-ray scans were carried out for each sample, with the data being processed separately as described above, and average peak heights calculated for each X-ray diffraction peak;

iii) the $K_{material}$ values were then determined for the recording materials of COMPARATIVE EXAMPLES 4 to 6 and INVENTION EXAMPLES 8 to 15 by adding up the average peak heights of the X-ray diffraction lines attributable to silver behenate at Bragg angles, 2Θ, of 6.01°, 7.56°, 9.12°, 10.66°, 12.12° and 13.62°;

iv) the $K_{1976}$ value was determined for NIST standard 1976 by adding up the average peak heights of the X-ray diffraction lines at Bragg angles, 2Θ, of 25.60°, 35.16° and 43.40°;

v) the weights of silver, $C_{Ag}$, present in 1 m² of the recording materials of COMPARATIVE EXAMPLES 4 to 6 and INVENTION EXAMPLES 8 to 15 were determined using a PHILIPS PW2400 wavelength dispersive X-ray fluorescence apparatus with a copper $K_\alpha$ X-ray source operating at 60 keV and a current of 50 mA, which had been calibrated for silver using silver-containing samples for which the silver concentrations had been determined using standard volumetric titration techniques; and vi) the crystallinity values for the silver behenate present in the recording materials of COMPARATIVE EXAMPLES 4 to 6 and INVENTION EXAMPLES 8 to 15 were determined using the expression: $K_{material}/(K_{1976} \times C_{Ag})$.

The crystallinity values for the silver behenate present in the recording materials of COMPARATIVE EXAMPLES 4 to 6 and INVENTION EXAMPLES 8 to 15 are summarized in tables 3 and 4 respectively.

TABLE 3

| Comparative example | silver behenate | | PVB | R01 | TA01 | TA02 | Oil | S01 | S02 | S03 |
|---|---|---|---|---|---|---|---|---|---|---|
| nr | Type | Crystallinity | [g/m²] | [g/m²] | [g/m²] | [g/m²] | [g/m²] | [g/m²] | [g/m²] | [g/m²] |
| 4 | A | 0.71 | 5.426 | 21.70 | 1.111 | 0.297 | 0.152 | 0.048 | 0.173 | 0.390 | 0.144 |
| 5 | B | 0.72 | 5.277 | 21.11 | 1.080 | 0.289 | 0.148 | 0.047 | 0.169 | 0.379 | 0.140 |
| 6 | C | 0.65 | 5.953 | 23.81 | 1.218 | 0.326 | 0.167 | 0.053 | 0.191 | 0.427 | 0.158 |

TABLE 4

| Invention example | silver behenate | | PVB | R01 | TA01 | TA02 | Oil | S01 | S02 | S03 |
|---|---|---|---|---|---|---|---|---|---|---|
| nr | Type | Crystallinity | [g/m²] | [g/m²] | [g/m²] | [g/m²] | [g/m²] | [g/m²] | [g/m²] | [g/m²] |
| 8 | I | 1.57 | 4.978 | 19.91 | 1.019 | 0.272 | 0.140 | 0.045 | 0.159 | 0.357 | 0.133 |
| 9 | I | 1.04 | 5.136 | 20.54 | 1.051 | 0.281 | 0.144 | 0.046 | 0.164 | 0.369 | 0.137 |
| 10 | II | 1.54 | 5.031 | 20.12 | 1.030 | 0.275 | 0.141 | 0.045 | 0.161 | 0.361 | 0.134 |
| 11 | III | 1.42 | 4.820 | 19.28 | 0.987 | 0.264 | 0.135 | 0.043 | 0.154 | 0.346 | 0.128 |
| 12 | IV | 1.68 | 4.978 | 19.91 | 1.019 | 0.264 | 0.140 | 0.045 | 0.159 | 0.357 | 0.133 |
| 13 | V | 1.68 | 4.899 | 19.60 | 1.003 | 0.268 | 0.138 | 0.044 | 0.157 | 0.352 | 0.130 |
| 14 | VI | 1.00 | 4.820 | 19.28 | 0.987 | 0.264 | 0.135 | 0.043 | 0.154 | 0.346 | 0.128 |
| 15 | VII | 1.58 | 5.479 | 21.92 | 1.121 | 0.300 | 0.154 | 0.049 | 0.175 | 0.447 | 0.146 |

Thermographic Printing

The printer was equipped with a thin film thermal head with a resolution of 300 dpi and was operated with a line time of 19 ms (the line time being the time needed for printing one line). During the line time the print head received constant power. The average printing power, being the total amount of electrical input energy during one line time divided by the line time and by the surface area of the heat-generating resistors was 1.5 mJ/dot being sufficient to obtain maximum optical density in each of the recording materials. During printing the print head was separated from the imaging layer by a thin intermediate material contacted with a slipping layer of a separable 5 μm thick polyethylene terephthalate ribbon coated successively with a subbing layer, heat-resistant layer and the slipping layer (anti-friction layer) giving the ribbon with a total thickness of 6 μm.

Image Evaluation

The optical maximum and minimum densities of the prints obtained with the recording materials of COMPARATIVE EXAMPLES 4 to 6 and INVENTION EXAMPLES 8 to 15 measured through a visual filter with a Macbeth™ TR924 densitometer for grey scale steps corresponding to data levels of 255 and 0 respectively are given in tables 5 and 6.

Image Tone Assessment

The image tone was determined by first printing recording materials which had been tempered for 7 days at 45° C. as described above and then subjecting the prints to visual inspection and to measurement of the b* CIELAB-value of the image as a function of image density as determined with a MACBETH™ TR924 densitometer. The L*, a* and b* CIELAB-values were determined by spectrophotometric measurements according to ASTM Norm E179-90 in a R(45/0) geometry with evaluation according to ASTM Norm E308-90. The visually assessed image tone and the b* value at the minimum in the dependence of b* upon image density for the recording materials of COMPARATIVE EXAMPLES 4 to 6 and INVENTION EXAMPLES 8 to 15 are also summarized in tables 5 and 6 respectively.

TABLE 5

| Comparative example number | AgB type | print characteristics | | | |
|---|---|---|---|---|---|
| | | $D_{max}$ | $D_{min}$ | image tone from visual inspection | b* at minimum in b* vs OD |
| 4 | A | 3.39 | 0.07 | brown | −0.1 |
| 5 | B | 3.48 | 0.07 | brown | −0.4 |
| 6 | C | 2.84 | 0.09 | brown | −1.5 |

TABLE 6

| Invention example number | AgB type | print characteristics | | | |
|---|---|---|---|---|---|
| | | $D_{max}$ | $D_{min}$ | image tone from visual inspection | b* at minimum in b* vs OD |
| 8 | I | 3.21 | 0.07 | blue | −4.3 |
| 9 | I | 2.82 | 0.07 | blue | −3.4 |
| 10 | II | 3.13 | 0.07 | blue/red | −4.8 |
| 11 | III | 2.81 | 0.07 | blue | −4.0 |
| 12 | IV | 2.81 | 0.07 | blue | −3.3 |
| 13 | V | 3.32 | 0.07 | blue/red | −3.0 |
| 14 | VI | 2.57 | 0.07 | blue | −3.7 |
| 15 | VII | 2.86 | 0.08 | blue | −5.1 |

The recording materials of COMPARATIVE EXAMPLES 4 to 6 with silver behenate types A to C all exhibited prints with a brown tone and a b* value at the minimum in the b* dependence upon image density of greater than −2.0, whereas the recording materials of INVENTION EXAMPLES 8 to 15 with silver behenate types I to VII prepared according to the present invention exhibited prints with a blue or blue/red tone and a b* value at the minimum in the b* dependence upon image density of less than −2.0.

COMPARATIVE EXAMPLES 7 & 8

The crystallinity and visual tone of silver behenate in samples of THERMALRES™ FILM type PR-PM-film lot number 04673456 a thermographic recording material based on a silver behenate-reducing-agent system from LABELON, COMPARATIVE EXAMPLE 7, and of DRY-VIEW™ 39701 DVB (blue) lot number 021132-013-A-025 a photothermographic recording material based on a silver behenate-reducing agent system from IMATION, COMPARATIVE EXAMPLE 8, was determined as described for INVENTION EXAMPLES 8 to 15 and COMPARATIVE EXAMPLES 4 to 6 and the results are summarized in table 7. Visual inspection of the silver behenate in the case of DRYVIEW™ 39701 DVB (blue) is not possible due to the use of a blue support.

TABLE 7

| Comparative Example number | Recording material | Crystallinity | image tone from visual inspection |
| --- | --- | --- | --- |
| 7 | THERMALRES ™ PR-PM-Film | 0.46 | brown |
| 8 | DRYVIEW ™ 39701 (blue) | 0.50 | not possible |

COMPARATIVE EXAMPLE 9
Thermographic Recording Material Incorporating Silver Behenate Produced According to the Teaching of EP-A 754 969

A sodium behenate solution was prepared by first dissolving 34 kg of behenic acid in 340 L of 2-propanol at 65° C. and then adding with stirring a 0.25N solution of sodium hydroxide until a solution pH of 8.7 was obtained. This required about 400 L of 0.25N NaOH. The concentration of the resulting solution was then adjusted to a sodium behenate concentration of 8.9% by weight and a concentration of 2-propanol in the solvent mixture of 16.7% by volume, by a combination of evaporation and dilution.

The silver behenate synthesis was carried out at a constant UAg of 400 mV as follows: to a stirred solution of 30 g of gelatin (type 7598 from AGFA GELATINFABRIK vorm. KOEPFF & SOEHNE) in 750 mL of distilled water at 72° C. in a double walled reactor, several drops of a 2.94M aqueous solution of silver nitrate were added to adjust the UAg at the start of the reaction to 400 mV and then 374 mL of the sodium behenate solution, whose preparation is described above, at a temperature of 78° C. was metered into the reactor at a rate of 46.6 mL/min and simultaneously a 2.94M aqueous solution of silver nitrate was metered into the reactor, its addition rate being controlled by the quantity of the silver nitrate solution necessary to maintain a UAg of 400±5 mV in the dispersing medium in the reactor. Both the sodium behenate and silver nitrate solutions were added to the dispersing medium via small diameter tubes positioned just under the surface of the dispersing medium. By the end of the addition step 0.092 moles of sodium behenate and 0.101 moles of silver nitrate had been added. The mixture was then stirred for a further 30 minutes. The resulting silver behenate dispersion contained 3.13% by weight of silver behenate and 2.28% by weight of K7598.

0.032 g of TA03, 2 g of a 20% by weight aqueous dispersion of LATEX 01 and tenside were added with stirring to 15 g of this silver behenate dispersion and the resulting dispersion diluted with demineralized water to a weight of 18.8 g before coating at a temperature of 40° C., using a doctor blade coater with a slit-width of 120 μm, onto a subbed 100 μm thick polyester sheet and dried. The dried layer consisted of: ca. 3 g/m² silver behenate, ca. 2.5 g/m² of LATEX 01, ca. 2.2 g/m² of K7598 and ca. 0.2 g/m² of TA03.

The crystallinity of the silver behenate in the thermographic material was determined as described for INVENTION EXAMPLES 8 to 15 and COMPARATIVE EXAMPLES 4 to 6 to be 0.33.

INVENTION EXAMPLES 16 to 20
Preparation of Silver Behenate Dispersions in an Aqueous Medium in the Absence of Organic Solvent Using a Single Jet Process Aqueous dispersions of the silver behenate types VIII to XII of INVENTION EXAMPLES 16 to 20 were produced as follows:

i) dispersing 102.18 g (0.3M) behenic acid with stirring at 400 rpm with a 100 mm diameter typhoon stirrer in a 250 mm in diameter vessel at 80° C. in a quantity of mL of a 10% solution of Surfactant nr 1/g behenic acid (see table 8) made up to 1 L with deionized water at a temperature of 80° C.;

ii) then adding 150 mL of a 2M aqueous solution of sodium hydroxide with stirring at 400 rpm with a 100 mm diameter typhoon stirrer to the 250 mm in diameter vessel at 80° C. over a period of 10 to 20 minutes to clear solution substantially containing sodium behenate;

iii) then adding a 300 mL of a 1M (or 100 mL of 3M in cases of INVENTION EXAMPLES 17 & 18) aqueous solution of silver nitrate with stirring at 400 rpm with a 100 mm diameter typhoon stirrer to the 250 mm in diameter vessel at a temperature of 80° C. at a particular rate of moles/moles silver behenate.min (see table 8 for the value for the particular silver behenate type), to convert the sodium behenate completely into silver behenate; and iv) ultrafiltration with a 500000 MW polysulfone cartridge filter at room temperature cassette to concentrate the resulting silver behenate dispersion (final AgB-concentration and residual conductivity in mS/cm are given in table 8).

The volume average particle size as determined by a Coulter LS230 diffractometer is also given in table 8.

TABLE 8

| Invention example number | AgB type | Surfactant type | mL 10% sol./ g HBeh | Temperature [° C.] | mol AgNO₃/mol AgB · min | ultrafiltration residual conductivity [mS/cm] | % AgB dispersion | average particle size [μm] |
| --- | --- | --- | --- | --- | --- | --- | --- | --- |
| 16 | VIII | nr 1 | 2.28 | 80 | 0.0625 | 4.9 | 23.3 | 0.433 |
| 17 | IX | nr 1 | 2.28 | 80 | 0.0625 | 4.3 | 18.9 | |
| 18 | X | nr 1 | 2.28 | 80 | 2.25 | | 14.11 | 0.111 |

TABLE 8-continued

| Invention example number | AgB type | Surfactant type | mL 10% sol./ g HBeh | Temperature [° C.] | mol AgNO$_3$/mol AgB · min | ultrafiltration residual conductivity [mS/cm] | % AgB dispersion | average particle size [μm] |
|---|---|---|---|---|---|---|---|---|
| 19 | XI | nr 1 | 4.56 | 80 | 0.0625 | 6.2 | 14.0 | 0.187 |
| 20 | XII | nr 1 | 4.56 | 80 | 0.157 | 6.5 | 14.0 | 0.135 |

These dispersions of silver behenate were directly used in the preparation of thermographic recording materials comprising thermographic elements coated from aqueous media.

Toning Agent Dispersions toner dispersion 01: dispersion of TA01 in an aqueous solution of Surfactant Nr 1 containing 30% of TA01 and 3% of Surfactant Nr. 1 (added as a dispersion);

toner dispersion 02: dispersion of TA02 in a gelatin solution containing 20% of K7598 (gelatin) and 10% of TA02 (added as flakes).

Preparation of Thermographic Recording Materials with the Aqueous Silver Behenate-Dispersions The thermographic recording materials of INVENTION EXAMPLES 16 to 20 were prepared by first dissolving K7598 in deionized water at 36° C. (see table 9 for quantities), then adding the appropriate Surfactant nr 1-containing silver behenate emulsion (see table 9 for quantity and concentration), then an aqueous dispersion of LATEX 02 with a pH of 5.0 (for quantity see table 9) followed by 5 minutes stirring, then an aqueous toner dispersion (for number and quantity, see table 9), while keeping the dispersion at 36° C. followed by vigorous stirring, then 6.3 g of toner dispersion 02 (see INVENTION EXAMPLES 16 to 20), then 11.23 g of a 13.7% by weight solution of R01 in ethanol and finally 1.31 g of a 3.66% by weight aqueous solution of formaldehyde.

TABLE 9

| Invention example number | water [g] | K7598 [g] | AgB disp. conc [%] | wt. [g] | Polymer 1 conc [%] | wt. [g] | toner disp. nr | wt. [g] |
|---|---|---|---|---|---|---|---|---|
| 16 | 22.66 | 2.25 | 23.25 | 19.36 | 30 | 5.58 | 01 | 3.61 |
| 17 | 10.58 | 2.26 | 18.9 | 23.68 | 30 | 5.57 | 02 | 5.38 |
| 18 | 10.12 | 2.25 | 14.11 | 31.90 | 30 | 5.58 | 01 | 3.61 |
| 19 | 9.90 | 2.25 | 14.0 | 32.13 | 30 | 5.58 | 01 | 3.61 |
| 20 | 9.82 | 2.25 | 14.0 | 32.20 | 30 | 5.58 | 01 | 3.61 |

The resulting silver behenate emulsions were then doctor blade-coated onto a 175 μm thick subbed polyethylene terephthalate support to produce the coating weights of silver given in table 10.

The crystallinity of the silver behenate in the thermographic recording materials of INVENTION EXAMPLES 16 to 20 were determined as described for INVENTION EXAMPLES 8 to 15 and COMPARATIVE EXAMPLES 4 to 6 and are given in table 10.

The thermographic recording materials of INVENTION EXAMPLES 16 to 20 and COMPARATIVE EXAMPLE 7 were printed and the prints evaluated as described for INVENTION EXAMPLES 8 to 15 and COMPARATIVE EXAMPLES 4 to 6. The maximum and minimum densities of the prints obtained with the thermographic recording materials of INVENTION EXAMPLES 16 to 20 measured through a blue filter with a Macbeth™ TR924 densitometer for grey scale steps corresponding to data levels of 255 and 0 respectively are also given in table 10.

Archivability Test

The achivability of prints made with the thermographic recording materials of INVENTION EXAMPLES 16 to 20 and COMPARATIVE EXAMPLE 7 was evaluated on the basis of the observed changes in minimum density upon heating the prints at 57° C. in a relative humidity (RH) of 34% for 3 days in the dark. The results of these tests are given in table 10.

Light Box Test

The stability of the image background of the prints made with the thermographic recording materials of INVENTION EXAMPLES 16 to 20 and COMPARATIVE EXAMPLE 7 was evaluated on the basis of the change in minimum (background) density measured through a blue filter using a MacBeth™ TR924 densitometer upon exposure on top of the white PVC window of a specially constructed light-box placed for 3 days in a Votsch conditioning cupboard set at 30° C. and a relative humidity (RH) of 85%. Only a central area of the window 550 mm long by 500 mm wide was used for mounting the test materials to ensure uniform exposure.

The stainless steel light-box used was 650 mm long, 600 mm wide and 120 mm high with an opening 610 mm long and 560 mm wide with a rim 10 mm wide and 5 mm deep round the opening, thereby forming a platform for a 5 mm thick plate of white PVC 630 mm long and 580 mm wide, making the white PVC-plate flush with the top of the light-box and preventing light loss from the light-box other than through the white PVC-plate. This light-box was fitted with 9 Planilux TLD 36 W/54 fluorescent lamps 27 mm in diameter mounted length-wise equidistantly from the two sides, with the lamps positioned equidistantly to one another and the sides over the whole width of the light-box and with the tops of the fluorescent tubes 30 mm below the bottom of the white PVC plate and 35 mm below the materials being tested.

The results of the light box tests are also given in table 10. The silver behenate in the thermographic recording materials of INVENTION EXAMPLES 16 to 20 exhibit high to very high crystallinities, according to the present invention, and the thermographic recording materials with these silver behenate particles with high to very high crystallinity exhibit minimum densities which are hardly changed upon being subjected to archivability and light box tests the present invention.

TABLE 10

| | Silver behenate coating | | | fresh print characteristics | | $\Delta D_{min}$ (blue) archivability | $\Delta D_{min}$ (blue) light box |
|---|---|---|---|---|---|---|---|
| | type | weight [g/m$^2$] | crystallinity | $D_{max}$ (blue) | $D_{min}$ (blue) | (3d/57° C./ 34% RH) | (3d/30° C./ 85% RH) |
| Comparative example number 7 | | | 0.46 | >4.0 | 0.10 | +0.83 | +0.02 |
| Invention example number | | | | | | | |
| 16 | VIII | 2.86 | 5.39 | 4.41 | 0.14 | −0.01 | 0.03 |
| 17 | IX | 3.98 | 1.76 | 3.56 | 0.11 | +0.01 | 0.04 |
| 18 | X | 3.61 | 3.20 | 3.27 | 0.12 | −0.03 | −0.01 |
| 19 | XI | 3.82 | 7.30 | 3.02 | 0.11 | −0.01 | 0.00 |
| 20 | XII | 4.19 | 1.92 | 3.16 | 0.13 | −0.02 | −0.01 |

INVENTION EXAMPLE 21

The photothermographic recording material of INVENTION EXAMPLE 21 produced using a silver behenate dispersion prepared by first preparing a predispersion by adding 56.5 g of the dried silver behenate powder type II of INVENTION EXAMPLE 2 to a solution of 56.5 g of PVB in 413.1 g of 2-butanone and then stirring for 10 minutes with an Ultra-Turrax™ stirrer. This predispersion was then microfluidized by passing it once through a MICROFLUIDICS™ M-110Y pressure microfluidizer at a jet pressure of 400 bar to produce 74% by weight dispersion of silver behenate in 2-butanone.

A photothermographic coating dispersion was then obtained by mixing 43.326 g of the silver behenate dispersion with 48.959 g of a 30% by weight solution of PVB for 20 minutes, 0.145 g of potassium iodide followed by 15 minutes stirring, 0.934 g of a 2-butanone solution containing 30% by weight of TA01 and 15.4% by weight of TA02 followed by 20 minutes stirring, 0.441 g of a 10% by weight solution of Oil in 2-butanone followed by 20 minutes stirring and 0.351 g of S02 followed by 20 minutes stirring. To this dispersion was then added with stirring a solution of 0.997 g of R01, 0.078 g of S01 and 0.130 g of S03. The resulting coating dispersion was then doctor blade-coated to a wet thickness of 120 μm onto a subbed polyethylene terephthalate support having a thickness of 175 μm to obtain, after drying for 1 hour at 50° C., a photothermographic recording material with a silver behenate coating weight of 4.31 g/m$^2$ and a silver iodide coating weight of 0.19 g/m$^2$.

The crystallinity of the silver behenate in the photothermographic recording materials of INVENTION EXAMPLE 21 was determined as described for INVENTION EXAMPLES 8 to 15 and COMPARATIVE EXAMPLES 4 to 6 to be 1.16.

The photothermographic recording material INVENTION EXAMPLE 21 was then exposed to ultra-violet light through a test original in contact with the material in an Agfa-Gevaert™ DL 1000 exposure apparatus followed by heating on a heated metal block for 5 s at 100° C. to produce a good image.

INVENTION EXAMPLE 22

The photothermographic recording material of INVENTION EXAMPLE 22 was produced using a silver behenate dispersion prepared as described in INVENTION EXAMPLE 20 for silver behenate type XII except that no ultrafiltration was carried out and that the concentration of silver behenate in the dispersion was 8.15% by weight instead of 14.0% by weight.

A photothermographic coating dispersion was then obtained by mixing with stirring 7.5 g of the silver behenate dispersion with 4 g of an 0.44% by weight aqueous solution of potassium iodide, then 2 g of a 20% by weight aqueous dispersion of LATEX 02, then 0.64 g of a 5.6% by weight aqueous solution of phthalazine and finally with 2 g of a 5.6% by weight aqueous solution of R02. The resulting coating dispersion was then doctor blade-coated to a wet thickness of 120 μm onto a subbed polyethylene terephthalate support having a thickness of 100 μm to obtain, after drying for 1 hour at 50° C., a photothermographic recording material with a silver behenate coating weight of 3.28 g/m$^2$ and a silver iodide coating weight of 0.12 g/m$^2$.

The crystallinity of the silver behenate in the photothermographic recording materials of INVENTION EXAMPLE 23 was determined as described for INVENTION EXAMPLES 8 to 15 and COMPARATIVE EXAMPLES 4 to 6 to be 1.10.

The photothermographic recording material of INVENTION EXAMPLE 22 was then exposed to ultra-violet light through a test original in contact with the material in an Agfa-Gevaer™ DL 1000 exposure apparatus followed by heating on a heated metal block for 5 s at 100° C. to produce a very good image with a high contrast.

INVENTION EXAMPLE 23

The photothermographic recording material of INVENTION EXAMPLE 23 was produced using the silver behenate dispersion described in INVENTION EXAMPLE 22. A photothermographic coating dispersion was then obtained as described for INVENTION EXAMPLE 22 except that 4 g of 0.97% by weight aqueous solution of calcium iodide was used instead of 4 g of an 0.44% by weight aqueous solution of potassium iodide. The resulting coating dispersion was then doctor blade-coated to a wet thickness of 120 μm onto a subbed polyethylene terephthalate support having a thickness of 100 μm to obtain, after drying for 1 hour at 50° C., a photothermographic recording material with a silver behenate coating weight of 3.17 g/m$^2$ and a silver iodide coating weight of 0.11 g/m$^2$.

The crystallinity of the silver behenate in the photothermographic recording materials of INVENTION EXAMPLE 23 was determined as described for INVENTION EXAMPLES 8 to 15 and COMPARATIVE EXAMPLES 4 to 6 to be 1.22.

The photothermographic recording material INVENTION EXAMPLE 23 was then exposed and thermally developed as described above for INVENTION EXAMPLE 22 to produce a very good image with a high contrast.

INVENTION EXAMPLES 24 to 26
Enhancement of Silver Behenate Crystallinity in the Presence of Phosphonium Compounds The thermographic recording materials of INVENTION EXAMPLES 24 to 26 had a composition which differed from that of INVENTION EXAMPLE 10. Therefore, since the composition has an influence upon the image colour, the print characteristics of INVENTION EXAMPLES 24 to 26 are not directly comparable with that of INVENTION EXAMPLE 10.

The thermographic recording materials of INVENTION EXAMPLES 24 to 26 were produced using a silver behenate dispersion prepared by first preparing a predispersion by adding 56.5 g of the dried silver behenate powder type II of INVENTION EXAMPLE 2 to a solution of 56.5 g of PVB in 413.1 g of 2-butanone and then stirring for 10 minutes with an Ultra-Turrax™ stirrer. This predispersion was then microfluidized by passing it once through a MICROFLUIDICS™ M-110Y high pressure microfluidizer at a jet pressure of 400 bar to produce a 10.74% by weight dispersion of silver behenate in 2-butanone.

Coating of Recording Materials

A subbed polyethylene terephthalate support having a thickness of 175 μm was doctor blade-coated from a coating composition containing 2-butanone as a solvent using the above-described silver behenate dispersions and the additional ingredients given below so as to obtain thereon, after drying for 1 hour at 50° C., layers with the compositions given in Table 11 for the thermographic recording materials of INVENTION EXAMPLES 24 to 26.

The evaluation results are summarized in Table 12.

TABLE 12

| Invention example number | AgB crystal-linity | Phos-phonium compound | $D_{max}$ | $D_{min}$ | print characteristics image tone from visual inspection | b* at minimum in b* vs OD |
|---|---|---|---|---|---|---|
| 24 | 1.62 | — | 3.87 | 0.08 | | −0.9 |
| 25 | 2.25 | PC01 | 2.84 | 0.07 | blue | −3.3 |
| 26 | 2.57 | PC02 | 3.10 | 0.06 | blue | −2.4 |

For the thermographic recording materials of INVENTION EXAMPLES 24 to 26 with the same composition, the increase in crystallinity upon addition of the phosphonium compounds at a concentration of 8 mol % with respect to the silver behenate present brought about a, desirable for image tone, reduction in the b.-value at the minimum in b. versus OD characteristic.

INVENTION EXAMPLES 27 to 31

The thermographic recording materials of INVENTION EXAMPLES 27 to 31 were prepared using a silver behenate powder type XIII produced as described for INVENTION EXAMPLE 4 except that the addition time was 2.5 minutes instead of 1.5 minutes and the final % by weight of 2-butanone was 40.9 instead of 45. A silver behenate was prepared with the type XIV silver behenate powder by first preparing a predispersion by adding 56.5 g of the dried silver behenate powder type XIII to a solution of 56.5 g of PVB in 389.2 g of 2-butanone and stirring for 10 minutes with an Ultra-Turrax™ stirrer. This predispersion was then microfluidized by passing it once through a MICROFLUIDICS™ M-110Y high pressure microfluidizer at a jet pressure of 400 bar to produce a 11.25% by weight dispersion of silver behenate in 2-butanone.

TABLE 11

| Invention example nr | silver behenate Crystal-linity | PVB [g/m²] | R01 [g/m²] | Phosphonium compound type | [g/m²] | TA01 [g/m²] | TA02 [g/m²] | Oil [g/m²] | S01 [g/m²] | S02 [g/m²] | S03 [g/m²] |
|---|---|---|---|---|---|---|---|---|---|---|---|
| 24 | 1.62 | 5.27 | 21.1 | 1.07 | — | — | 0.32 | 0.16 | 0.047 | 0.08 | 0.38 | 0.14 |
| 25 | 2.25 | 4.56 | 18.3 | 0.93 | PC01 | 0.40 | 0.28 | 0.14 | 0.041 | 0.07 | 0.33 | 0.12 |
| 26 | 2.57 | 4.60 | 18.4 | 0.94 | PC02 | 0.38 | 0.28 | 0.14 | 0.041 | 0.07 | 0.33 | 0.12 |

The crystallinity values for the silver behenate present in the thermographic recording materials of INVENTION EXAMPLES 24 to 26 determined as described for COMPARATIVE EXAMPLES 4 to 6 and INVENTION EXAMPLES 8 to 15 are summarized in Table 12. It is clear from these results that the presence of the phosphonium compounds PC01 and PC02 has increased the crystallinity of the silver behenate in the recording materials of INVENTION EXAMPLES 25 & 26 over that of the silver behenate in the thermographic recording material of INVENTION EXAMPLE 24 with the same concentrations of the other ingredients.

Thermographic printing with the thermographic recording materials of INVENTION EXAMPLES 24 to 26 and the evaluation thereof were carried out as described for the thermographic recording materials of COMPARATIVE EXAMPLES 4 to 6 and INVENTION EXAMPLES 8 to 15.

A subbed polyethylene terephthalate support having a thickness of 175 μm was doctor blade-coated from a coating composition containing 2-butanone as a solvent using the above-described silver behenate dispersions and the additional ingredients given below so as to obtain thereon, after drying for 1 hour at 50° C., layers with the compositions given in Table 13 for the thermographic recording materials of INVENTION EXAMPLES 27 to 31.

The crystallinity values for the silver behenate present in the thermographic recording materials of INVENTION EXAMPLES 27 to 31 determined as described for COMPARATIVE EXAMPLES 4 to 6 and INVENTION EXAMPLES 8 to 15 are also summarized in Table 13.

TABLE 13

| Invention example nr | silver behenate Crystal- linity | [g/m$^2$] | PVB [g/m$^2$] | R01 [g/m$^2$] | PC01 mol % vs AgB | [g/m$^2$] | TA01 [g/m$^2$] | TA02 [g/m$^2$] | Oil [g/m$^2$] | S01 [g/m$^2$] | S02 [g/m$^2$] | S03 [g/m$^2$] |
|---|---|---|---|---|---|---|---|---|---|---|---|---|
| 27 | 1.52 | 3.90 | 15.6 | 0.79 | 0 | 0 | 0.24 | 0.12 | 0.035 | 0.062 | 0.28 | 0.10 |
| 28 | 1.78 | 4.07 | 16.3 | 0.83 | 2 | 0.09 | 0.25 | 0.13 | 0.037 | 0.065 | 0.29 | 0.11 |
| 29 | 1.86 | 3.90 | 15.6 | 0.79 | 4 | 0.17 | 0.24 | 0.12 | 0.035 | 0.062 | 0.28 | 0.10 |
| 30 | 1.82 | 3.94 | 15.8 | 0.80 | 6 | 0.26 | 0.24 | 0.12 | 0.035 | 0.063 | 0.28 | 0.10 |
| 31 | 1.64 | 4.27 | 17.1 | 0.87 | 8 | 0.38 | 0.26 | 0.13 | 0.038 | 0.068 | 0.31 | 0.11 |

It is evident from table 13 that the crystallinities of the silver behenate in the thermographic recording materials of INVENTION EXAMPLES 28 to 31 in which the phosphonium compound PC01 is present are higher than that of the silver behenate in the thermographic recording material of INVENTION EXAMPLE 27 and moreover that there is an increase in silver behenate crystallinity with increasing PC01-concentration up to a concentration of 4 to 6 mol % with respect to the silver behenate present.

Thermographic printing with the thermographic recording materials of INVENTION EXAMPLES 27 to 31 and the evaluation thereof were carried out as described for the thermographic recording materials of COMPARATIVE EXAMPLES 4 to 6 and INVENTION EXAMPLES 8 to 15. The evaluation results are summarized in Table 14.

TABLE 14

| | | | print characteristics | | | |
|---|---|---|---|---|---|---|
| Invention example number | AgB crystal- linity | mol % PC01 vs AgB | $D_{max}$ | $D_{min}$ | image tone from visual inspection | b* at minimum in b* vs OD |
| 27 | 1.52 | 0 | 2.50 | 0.06 | blue | −5.1 |
| 28 | 1.78 | 2 | 2.54 | 0.06 | blue | −4.25 |
| 29 | 1.86 | 4 | 2.66 | 0.07 | blue | −4.55 |
| 30 | 1.83 | 6 | 2.65 | 0.07 | blue | −4.7 |
| 31 | 1.64 | 8 | 2.94 | 0.07 | blue | −3.8 |

The results of table 14 for thermographic recording materials of INVENTION EXAMPLES 28 to 31 with the phosphonium compound PC01 in different concentrations show comparable b*-values at the minimum in b*versus OD characteristics to the thermographic recording material of INVENTION EXAMPLE 27 without a phosphonium compound.

Having described in detail preferred embodiments of the current invention, it will now be apparent to those skilled in the art that numerous modifications can be made therein without departing from the scope of the invention as defined in the following claims.

What is claimed is:

1. A process for producing particles of a substantially light-insensitive organic silver salt, said particles containing silver behenate, said process comprising:
   (i) preparing a solution or dispersion, A, containing an alkali metal or ammonium salt of an organic compound with at least one acidic hydrogen atom, said organic compound including behenic acid, said salt of the organic compound containing alkali or ammonium ions, in a mixture of water and an organic solvent, at a temperature at which particles of said substantially light-insensitive organic silver salt containing silver behenate do not undergo reduction; and
   (ii) adding a quantity of an aqueous solution, B, of a silver salt containing an equal number of silver ions to the alkali or ammonium ions in said solution or dispersion A;

wherein an initial mixing number during said addition of said aqueous solution B to said solution or dispersion A is greater than or equal to 2×10$^{-4}$ during said production of said particles of substantially light-insensitive organic silver salt containing silver behenate, said mixing number being defined as the ratio of the molar rate at which said silver salt is supplied to said solution or dispersion A in a reactor to the molar rate at which said alkali or ammonium salt of the organic compound is circulated in said reactor; and wherein said particles of the substantially light-insensitive organic silver salt, said particles containing silver behenate, are not associated with mercury and/or lead ions.

2. The process according to claim 1, wherein concentration of said alkali or ammonium salt in said solution or dispersion A is greater than 0.022 moles/L.

3. The process according to claim 1, wherein the organic solvent is present at between 20 and 80% by weight of said mixture of water and an organic solvent.

4. The process according to claim 1, wherein the organic solvent is present at between 35 and 65% by weight of said mixture of water and an organic solvent.

5. The process according to claim 1, wherein said solvent is 2-butanone.

6. The process according to claim 1, wherein at least 20% by weight of said particles are present as globular particles.

7. The process according to claim 1, wherein at least 40% by weight of said particles are present as globular particles.

8. A recording material, comprising:
   a support;
   a thermosensitive element containing particles of substantially light-insensitive organic silver salt, said particles containing silver behenate, produced by a process comprising:
   (i) preparing a solution or dispersion, A, comprising an alkali metal or ammonium salt of an organic compound, said organic compound including behenic acid, said salt of the organic compound containing alkali or ammonium ions, in a mixture of water and an organic solvent at a temperature at which particles of said substantially light-insensitive organic silver salt containing silver behenate do not undergo reduction; and
   (ii) adding a quantity of an aqueous solution, B, of a silver salt containing an equal number of silver ions to the alkali or ammonium ions in said solution or dispersion A;
wherein an initial mixing number during said addition of said aqueous solution B to said solution or dispersion A is greater than or equal to 2×10$^{-4}$ during said production of said particles of substantially light-insensitive organic silver salt containing silver behenate, said mixing number being defined as a ratio of the molar rate at which said silver salt is supplied to said solution or dispersion A in a reactor to the molar rate at which said alkali or ammonium salt is circulated in said reactor;

an organic reducing agent therefor in thermal working relationship therewith; and a binder;

wherein said particles of substantially light-insensitive organic silver salt containing silver behenate are not associated with mercury and/or lead ions, and wherein crystallinity of said silver behenate is greater than 1.20, said crystallinity being defined as a ratio of a sum of peak heights of X-ray diffraction lines attributable to silver behenate at Bragg angles, $2\Theta$, of 6.01°, 7.56°, 9.12°, 10.66°, 12.12° and 13.62° to a sum of peak heights of X-ray diffraction lines of NIST standard 1976, rhombohedral $Al_2O_3$, at Bragg angles, $2\Theta$, of 25.60°, 35.16° and 43.40°, being determined by irradiating the recording material with a copper $K\alpha_1$ source with the same X-ray diffractometer in the same state of adjustment, and normalized to a quantity of silver of 1 gram per $m^2$ of the recording material.

9. The recording material according to claim 8, wherein said thermosensitive element further contains a toning agent.

10. The recording material according to claim 8, wherein said thermosensitive element is provided with a protective layer.

11. The recording material according to claim 8, wherein said thermosensitive element further contains a photosensitive species capable upon exposure of forming a species capable of catalyzing reduction of said silver behenate.

12. A recording process, comprising:

(A) bringing an outermost layer of a recording material into proximity with a heat source, said recording material including a support;

a thermosensitive element, containing particles of substantially light-insensitive organic silver salt, said particles containing silver behenate, said thermosensitive element produced by a process comprising:

(i) preparing a solution or dispersion, A, containing an alkali metal or ammonium salt of an organic compound with at least one acidic hydrogen atom, said organic compound including behenic acid, said salt of the organic compound containing alkali or ammonium ions, in a mixture of water and an organic solvent at a temperature at which particles of said substantially light-insensitive organic silver salt containing silver behenate do not undergo reduction; and (ii) adding a quantity of an aqueous solution, B, of a silver salt containing an equal number of silver ions to the alkali or ammonium ions in said solution or dispersion A;

wherein an initial mixing number during said addition of said aqueous solution B to said solution or dispersion A is greater than or equal to $2\times10^{-4}$ during said production of said particles of substantially light-insensitive organic silver salt containing silver behenate, said mixing number being defined as a ratio of the molar rate at which said silver salt is supplied to said solution or dispersion A in a reactor to the molar rate at which said alkali or ammonium salt is circulated in said reactor;

an organic reducing agent therefor in thermal working relationship therewith; and a binder;

(B) applying heat from said heat source by imagewise heating of the recording material while maintaining proximity to said heat source to produce an image; and (C) removing said recording material from said heat source;

wherein said particles are not associated with mercury and/or lead ions.

13. The recording process according to claim 12, wherein said heat source is a thin film thermal head.

* * * * *